US008906430B2

(12) United States Patent
Mercati et al.

(10) Patent No.: US 8,906,430 B2
(45) Date of Patent: Dec. 9, 2014

(54) USE OF HYPERICUM PERFORATUM EXTRACTS IN THE TREATMENT OF NEUROPATHIC PAIN

(75) Inventors: Valentino Mercati, Sansepolcro (AR) (IT); Franco Francesco Vincieri, Florence (IT); Anna Rita Bilia, Bacchereto Carmignano (PO) (IT); Carla Ghelardini, Pistoia (IT); Nicoletta Galeotti, Poggibonsi (SI) (IT)

(73) Assignee: Aboca S.p.A. Societa' Agricola, Sansepolcro (IT)

( * ) Notice: Subject to any disclaimer, the term of this patent is extended or adjusted under 35 U.S.C. 154(b) by 378 days.

(21) Appl. No.: 13/111,386

(22) Filed: May 19, 2011

(65) Prior Publication Data

US 2011/0218249 A1 Sep. 8, 2011

Related U.S. Application Data

(62) Division of application No. 12/919,360, filed as application No. PCT/EP2009/001211 on Feb. 19, 2009, now abandoned.

(30) Foreign Application Priority Data

Feb. 27, 2008 (IT) .............................. MI2008A00316

(51) Int. Cl.
*A61K 36/38* (2006.01)
(52) U.S. Cl.
CPC ...................................... *A61K 36/38* (2013.01)
USPC ............................ 424/730; 424/778; 424/779
(58) Field of Classification Search
CPC ....................................................... A61K 36/38
USPC ............................................ 424/730, 778, 779
See application file for complete search history.

(56) References Cited

U.S. PATENT DOCUMENTS

| 6,197,823 | B1 | 3/2001 | Barr et al. | |
|---|---|---|---|---|
| 6,638,981 | B2 * | 10/2003 | Williams et al. | 514/656 |
| 2002/0090403 | A1 * | 7/2002 | Nishibe et al. | 424/725 |
| 2003/0207940 | A1 | 11/2003 | Shan et al. | |

FOREIGN PATENT DOCUMENTS

| WO | WO 99/64027 A1 | 12/1999 |
|---|---|---|
| WO | WO 2005/117924 A1 | 12/2005 |

OTHER PUBLICATIONS

EMEA report (The European Agency for the Evaluation of Medicinal Products; Veterinary Medicines Evaluation Unit: Hyperici Oleum: Summary Report (1998)).*
Puri (Journal of Chromatographic Science (2006), vol. 44, pp. 177-180).*
http://www.patient.co.uk/health/Neuropathic-Pain.htm—accessed Jul. 2012.*
Polomano (Pain (2001), vol. 94, pp. 293-304).*
Forman (Current Oncology Reports (2004), vol. 6, pp. 20-25).*
Head (Alternative Medicine Review (2006), vol. 11, No. 4, pp. 294-329).*
Cirak Cuneyt et al., "Variation of Bioactive Compounds in *Hypericum perforatum* Growing in Turkey During its Phenological Cycle", Journal of Integrative Plant Biology, May 2007, pp. 615-620, vol. 49, nr. 5.
Butterweck V et al., "Pharmacological and Endocrine Effects of *Hypericum perforatum* and Hypericin After Repeated Treatment", Pharmacopsychiatry, Jul. 2001, pp. S2-S7, vol. 34, Nr. S1.
Lou Galantino M et al., "Complementary and Alternative Medicine Interventions for the Orthopedic Patient: A Review of the Literature", Seminars in Integrative Medicine, Jun. 1, 2003, pp. 65-79, Elsevier, US.
Butterweck V et al., "Effects of the Total Extract and Fractions of *Hypericum perforatum* in Animal Assays for Antidepressant Activity", Georg Thieme Verlag, Sep. 30, 1997, pp. 117-124, vol. 30, No. suppl. 2, Stuttgart, DE.
Reuter H D, Phytotherapie An Der Schwelle Des Neuen Jahrtausends = Phytotheraphy at the Threshold of the New Millennium. Report on the $10^{th}$ Annual Meeting of the Society for Phytotherapy, Nov. 11-13, 1999 in Munster, Zeitschrift Fuer Phytotherapie, Jan. 1, 2000, pp. 87-97, 100, vol. 21, No. 2, Stuttgart, DE.
Rezvani A H et al., "Attenuation of Alcohol Intake by Extract of *Hypericum perforatum* (St. John's Wort) in two Different Strains of Alcohol-Preferring Rats", Alcohol and Alcoholism, Sep. 1, 1999, pp. 699-705, vol. 34, No. 5, Pergamon, Oxford, GB.
Mohammad Azam Khan; Ikseer Azam, vol. IV ($19^{th}$ century AD), Matba Nizami, Kanpur, 1872 AD.
Abu Ali Ibn-e-Sina; Al-Qaanoon-fil-Tibb, vol. II ($11^{th}$ century AD), Institute of History of Medicine and Medical Research, Jamia Hamdard, New Delhi—62, 1987 AD.
Abu Bakr Mohammad.Bin Zakariyya Al-Razi; Kitaab-al-Haawi-fil-Tibb, vol. XI ($5^{th}$ century AD), Dayerah-al-Ma'aarif Usmania Hyderabad (First Edition) 1962 AD.
Mohammad Najmul Ghani Khan; Qaraabaadeen Najm-al-Ghani ($20^{th}$ century AD), Munshi Nawal Kishore, Lucknow, (Second Edition) 1928 AD.
Abu Bakr Mohammad.Bin Zakariyya Al-Razi; Kitaab-al-Haawi-fil-Tibb, vol. X1 ($9^{th}$ century AD), Dayerah-al-Ma'aarif Usmania, Hyderabad, (First Edition) 1962 AD.
Abu Bakr Mohammad. Bin Zakariyya Al-Razi; Kitaab-al-Haawi-fil-Tibb, vol. XI ($9^{th}$ century AD), Dayerah-al-Ma'aarif Usmania, Hyderabad, (First Edition) 1962 AD.
Galeotti et al. "St. John's wort reduces neuropathic pain through a *Hypericin*-mediated inhibition of the protein kinase C γ and ε activity" *Biochem. Pharmacol.* 79:1327-1336 (May 2010).
Hölzl & Petersen "Chemical constituents of *Hypericum*" in *Hypericum: The Genus Hypericum* (Ernst, ed.), CRC Press, p. 84 (Jan. 2003).
Moore et al. "St. John's wort induces hepatic drug metabolism through activation of the pregnane X receptor" *Proc. Natl. Acad. Sci. USA* 97:7500-7502 (Jun. 2000).
Mueller et al. "No clinically relevant CYP3A induction after St. John's wort with low hyperforin content in healthy volunteers" *Eur. J. Clin. Pharmacol.* 65:81-87 (Jan. 2009).
Sindrup et al. "St. John's wort has no effect on pain in polyneuropathy" *Pain* 91:361-365 (Apr. 2001).

* cited by examiner

*Primary Examiner* — Susan Hoffman
(74) *Attorney, Agent, or Firm* — Nixon & Vanderhye PC

(57) ABSTRACT

Disclosed is the use of *hypericum* (*Hypericum perforatum* L.) tip extracts containing hypericin, of hypericin, to prepare medicinal products and/or food supplements for the treatment of neuropathic pain.

15 Claims, 2 Drawing Sheets

USE OF HYPERICUM PERFORATUM EXTRACTS IN THE TREATMENT OF NEUROPATHIC PAIN

CROSS-REFERENCE TO RELATED APPLICATIONS

This is a divisional application which claims the benefit of U.S. patent application Ser. No. 12/919,360, filed Sep. 15, 2010 now abandoned, which is a National Stage entry of International Application No. PCT/EP2009/001211, filed Feb. 19, 2009, and claims priority of Italian Patent Application No. MI 2008 A 000316, filed Feb. 27, 2008. The disclosures of the prior applications are hereby incorporated herein in their entirety by reference.

The present invention relates to the use of extracts of hypericum (*Hypericum perforatum* L.) flowering stems and the components thereof for the preparation of pharmaceutical preparations and/or food supplements for the treatment of various forms of neuropathic pain (caused by chemotherapy drugs, mononeuropathy or osteoarthritis).

BACKGROUND TO THE INVENTION

Pain is defined by the International Association for the Study of Pain (IASP) as "an unpleasant sensory and emotional experience associated with actual or potential tissue damage, or described in terms of such damage".

Within this definition a particular type of pain associated with neurological abnormalities, called neuropathic pain, is becoming increasingly important due to its significant, growing worldwide prevalence. Neuropathic pain is defined as "pain initiated or caused by a primary lesion or dysfunction in the nervous system", which may take the form of dysaesthesia, allodynia, hyperpathy, stinging or stabbing pain.

Neuropathic pain is distinguished from other types of commonly reported (nociceptive) pain, including headache, backache, and other types of musculoskeletal pain, and comprises a heterogeneous group of conditions which cannot be explained by a single etiology or a particular anatomical lesion.

These disorders of the structures of the central or peripheral nervous system include various neuropathies (diabetic neuropathy, post-herpetic neuropathy, inflammatory neuropathies, neuropathy caused by alcohol abuse and neuropathy associated with HIV/AIDS infection), and can derive from various toxins (such as neurotoxins), acute trauma (including surgical traumas), chronic trauma (such as repetitive stress syndrome), mononeuropathies, such as carpal tunnel syndrome (the most common type of mononeuropathy, which affects 2.8% to 4.6% of the adult population), and disorders of the central nervous system (such as stroke, multiple sclerosis, cerebral ischaemia, Parkinson's disease, spinal cord lesions and head injuries).

The disorder is not easy to diagnose, because although the nerve produces continual painful discharges, it is often anatomically intact.

Neuropathic pain covers a variety of pathological states and presents with a variety of symptoms, which have the following common denominators:
  pain is perceived in the absence of a permanent, identifiable tissue lesion or process;
  unpleasant, abnormal or unusual sensations (dysaesthesia) are present, frequently described as stinging or electric shocks;
  brief episodes of paroxystic stabbing or piercing pain are present;
  the pain appears some time after the lesion that triggered it
  the pain is perceived in a region with a sensory deficit;
  even mild stimuli are painful (allodynia);
  marked summation and persistent activity occur after the application of repeated stimuli.

It is estimated that neuropathic pain affects up to 3% of the population, and that some 1 to 5% of European adults suffer from chronic pain.

According to the literature, in the USA the problem of neuropathic pain is potentially onerous for the national insurance systems, with a prevalence of 1.5%.

80% of patients with tumours at an advanced stage present neuropathic symptoms.

Chronic neuropathic pain is a major problem in neurology because it is frequent and often disabling, due to its unpleasant, chronic nature.

It is also a type of pain which does not respond well to the most common analgesics, such as acetylsalicylic acid, paracetamol or the most common non-steroidal anti-inflammatory drugs.

The aim of pharmacological treatments should be to prevent pain, but in practice, the most that can be achieved is to reduce the pain to a bearable level.

At present, no class of drugs has proved universally effective for patients with neuropathic pain.

"Off-label" drugs belonging to the following categories are generally used, but cause serious side effects in the long term:
  antidepressants
  anticonvulsants (gabapentin)
  opioids (methadone, oxycodone)
  tramadol
  lidocaine
  cytokine-inhibiting anti-inflammatories.

When these drugs are effective, they reduce pain by 25-40% in 40-60% of patients.

Moreover, numerous adverse effects are caused by continuous use of these drugs.

Neuropathic pain therefore represents a major clinical challenge due to its severity, chronic nature, resistance to the usual treatments and serious effect on the quality of the life.

The main research into this disorder uses experimental metabolic, pharmacological or trauma models in rodents, which reproduce the characteristics of human pain symptoms (Ref 1-7).

*Hypericum*, also known as St. John's Wort, consists of the flowering stems of *Hypericum perforatum*. It contains a large number of different classes of substances: naphthodianthrone derivatives such as hypericin, pseudohypericin and isohypericin, and phloroglucinol derivatives such as hyperforin. It also contains flavonoids such as hyperoside, rutin, I3,II8-biapigenin, quercetin, quercitrin and isoquercitrin, procyanidins, essential oil and xanthones.

It is widely used in modern phytotherapy to treat some forms of mild or moderate depression and psychovegetative problems, with effective results at the dose of 500-1050 mg of extract/day divided into 2-3 doses, for 2-4 weeks, and fewer side effects than treatment with synthetic antidepressants.

*Hypericum perforatum* extracts have been tested in many experimental pharmacological and clinical trials, which fully support its use for depression, but many questions about its characteristics still remain unanswered. A number of action mechanisms have been suggested to explain its antidepressant effects: 1) non-selective serotonin, noradrenaline and dopamine reuptake inhibition; 2) increased density of the serotoninergic, dopaminergic and GABA receptors; 3) increased affinity for the GABA receptors; 4) inhibition of the enzyme monoamine oxidase (MAO). The identity of the active components is still in doubt, and its pharmacological activity seems to be complex and determined by the concomitant effects of a number of active substances. Hypericin has been identified as "the" active ingredient, but a new component, hyperforin, which was recently identified, seems to play an important part in the efficacy of the plant, while flavonoids, in particular rutin, have been identified as compounds which can influence its activity (Ref. 8-15).

A clinical trial (16) published in 2000 describes the inefficacy of a *hypericum* extract in the treatment of neuropathies.

Other studies describe the analgesic activity of *hypericum*, but they were conducted on different species from *Hypericum perforatum*, the extracts were not chemically characterised, the administration route was often not oral, and above all, they were evaluated on non-neuropathic pain models (hot plate test, writhing test, Ref. 16-22).

DESCRIPTION OF THE INVENTION

Freeze-dried extracts of *hypericum* (*Hypericum perforatum*) flowering stems and one of its components, hypericin, have proved effective in reducing the symptoms of neuropathic pain in various experimental models, following oral administration.

The studies were conducted on rodents, which have always constituted a good animal model to reproduce the characteristics of human pain symptoms and predict possible remedies.

The freeze-dried extracts can derive from freeze-drying of either the whole plant material extracted with water-ethanol solvent, or of the most hydrophilic component of the plant.

The active closes of freeze-dried *hypericum* extracts range from 10 mg/kg to 100 mg/kg.

The freeze-dried extracts preferably derive from extraction of the whole plant with water-alcohol solvents (0-100% ethanol, methanol, isopropanol, etc.) or water-acetone solvents (0-100%) and separation and freeze-drying of a more hydrophilic component from the plant.

Freeze-dried *hypericum* extracts preferably have a content of naphthodianthrone derivatives (hypericin+pseudohypericin) amounting to not less than 0.25%, evaluated by the HPLC method (minimum 0.025 mg per kg of body weight).

One of the naphthodianthrone derivatives, hypericin, has proved active at a dose corresponding to its concentration in freeze-dried extracts.

The phloroglucinol derivatives isolated (hyperforin and adihyperforin) have proved unable to reduce neuropathic pain.

Up to the dose of 3000 mg/kg per os the freeze-dried extract does not change the animal's behaviour, as demonstrated by the fact that the number of falls from the rotating rod consecutively declines as the sessions are repeated, demonstrating that the animals' motor coordination is wholly comparable to that of the controls (Ref. 29 Rota Rod test).

When analyzed in terms of numerous parameters (behaviour, movement, muscle tone, autonomic signs), the extracts did not cause any alteration. The scores of the treated animals did not differ from those of the controls (Ref. 28 Irwin test).

The invention is described in greater detail in the Examples and Preparations below.

Preparation 1. Total Freeze-Dried Extract

Figure 1:
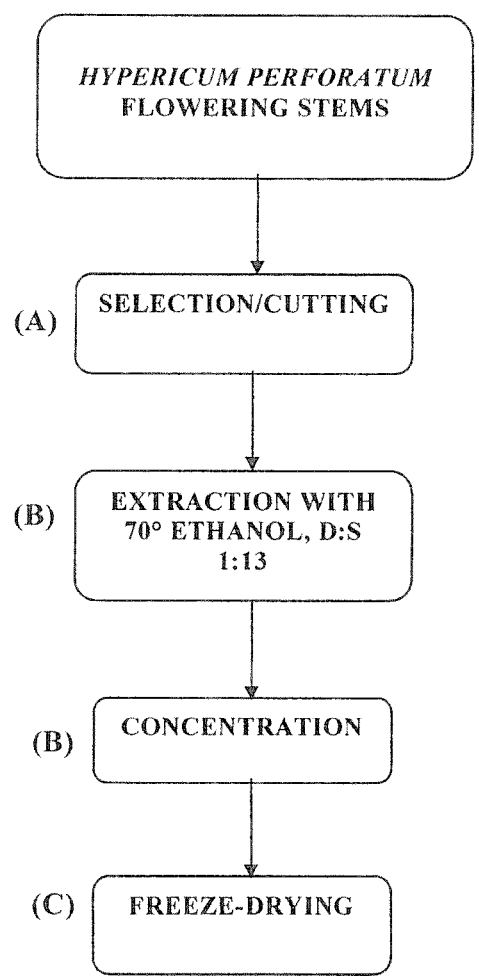
FIG. 1 shows a flow chart of a method of preparing total freeze-dried extracts.

FIG. 1 shows the flow chart of the preparation method.

The freeze-dried *hypericum* (*Hypericum perforatum*) flowering stem extract is prepared from *hypericum* flowering stems. After drying and selection of the tips, extraction is performed with a water-ethanol solution containing, 50-80% alcohol, with a plant:solvent ratio of 1:13.

The solution is concentrated under reduced pressure to remove the ethanol, and dried by a freeze-drying process in suitable freeze-dryers.

Preparation 2. Freeze-Dried Extract of the Hydrophilic Fraction

Figure 2:
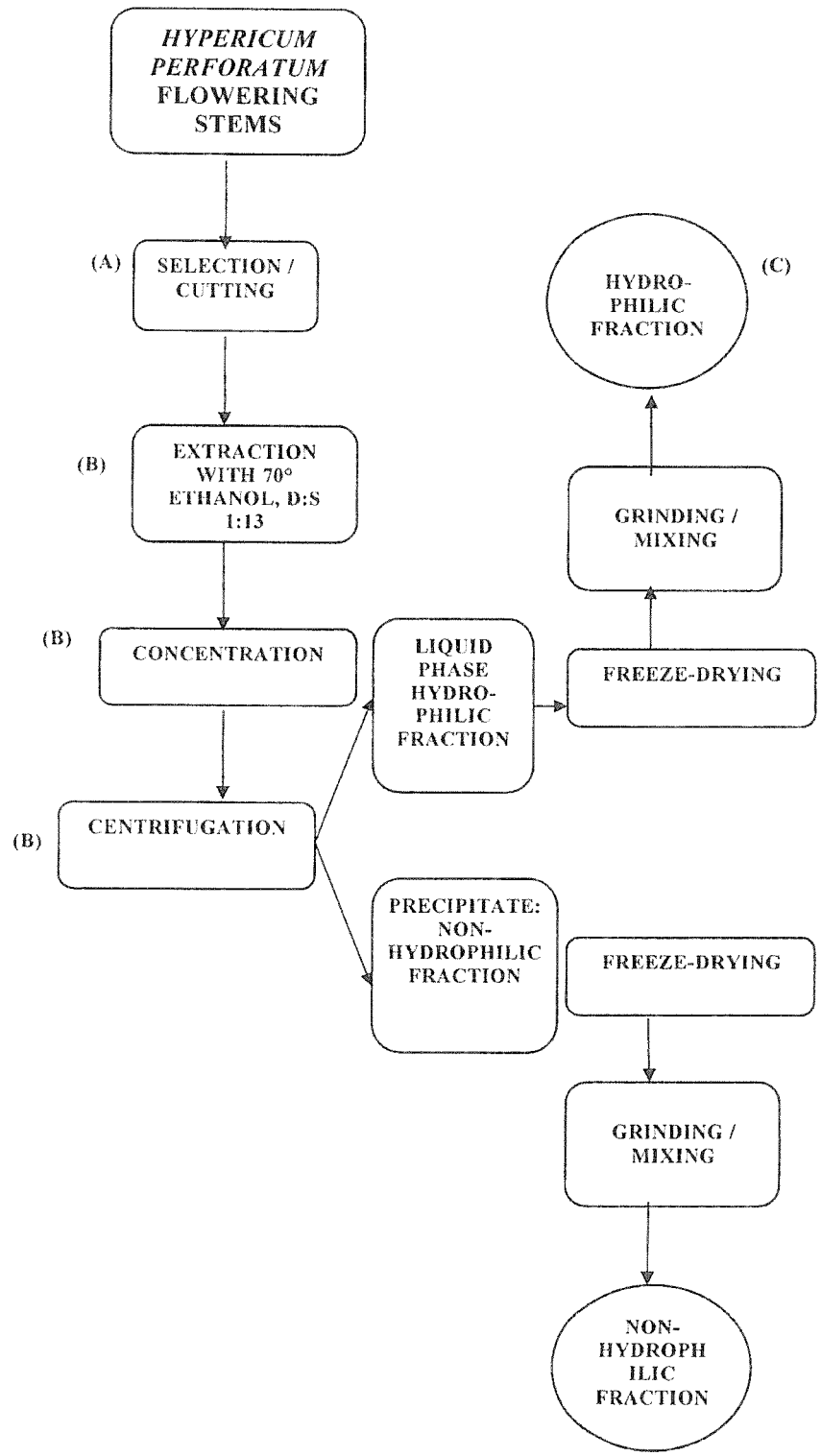
FIG. 2 shows a flow chart of a method of preparing freeze-dried extracts of a hydrophilic fraction of *hypericum*.

FIG. 2 shows the flow chart of the preparation method.

The freeze-dried extract of the hydrophilic fraction of *hypericum*, containing polar water-soluble substances, was prepared by a process of physical separation of the non-hydrophilic substances, and centrifugation with a decanter. The two fractions were then freeze-dried separately.

The freeze-dried extract was chemically characterised by HPLC analysis, which showed a total hypericin concentration (hypericin+pseudohypericin) of 0.27 to 0.37%.

Example 1

Oxaliplatin-Induced Neuropathy

A reduction in the pain threshold was induced by administering oxaliplatin 2.4 mg/kg for 5 consecutive days for a total of 3 weeks. By the end of the treatment period, the pain perception threshold of the rats was statistically lower than that of the controls (Ref. 23).

The total freeze-dried extract at the dose of 30 and 60 mg/kg of body weight proved to be active to a statistically significant extent.

TABLE 1a

DOSE-RESPONSE CURVE OF *HYPERICUM* EXTRACT ON OXALIPLATIN-INDUCED HYPERALGESIA IN THE RAT PAW PRESSURE TEST

| TREATMENT i.p. | TREATMENT MG/KG P.O. | Pressure on rats' paws (g) | | | |
|---|---|---|---|---|---|
| | | Pre-test | 3rd week + 15 min. | 3rd week + 30 min | 3rd week + 45 min |
| SALINE | CMC | 57.4 ± 3.5 | 61.8 ± 5.4 | 67.4 ± 6.3 | 62.3 ± 5.4 |
| OXALIPLATIN | CMC | 22.6 ± 4.6 | 25.1 ± 6.1 | 26.9 ± 5.4 | 24.3 ± 6.6 |
| OXALIPLATIN | *HYPERICUM* EXTRACT 30 mg/kg | 21.7 ± 1.2 | 58.1 ± 3.5* | 67.8 ± 2.0* | 29.1 ± 2.0 |
| OXALIPLATIN | *HYPERICUM* EXTRACT 60 mg/kg | 24.5 ± 1.3 | 48.2 ± 4.6* | 25.7 ± 2.4 | 21.5 ± 0.0 |

Oxaliplatin 2.4 mg/kg−1 for 5 consecutive days a week (15 i.p. injections - cumulative dose 36 mg/kg)

$\hat{}$ $p < 0.05$

*$p > 0.01$

The freeze-dried extract of the hydrophilic fraction at the dose of 30 mg/lag of body weight proved active to a statistically significant extent in the oxaliplatin-induced neuropathy pain test.

TABLE 1 b

DOSE-RESPONSE CURVE OF HYDROPHILIC FRACTION OF *HYPERICUM* EXTRACT ON OXALIPLATIN-INDUCED HYPERALGESIA IN THE RAT PAW PRESSURE TEST

| TREATMENT i.p. | TREATMENT MG/KG P.O. | Pressure on rats' paws (g) | | | |
|---|---|---|---|---|---|
| | | PRE-TEST | 3rd week + 15 min. | 3rd week + 30 min | 3rd week + 45 min |
| SALINE | CMC | 57.4 ± 3.5 | 61.8 ± 5.4 | 67.4 ± 6.3 | 62.3 ± 5.4 |
| OXALIPLATIN | CMC | 22.6 ± 4.6 | 25.1 ± 6.1 | 26.9 ± 5.4 | 24.3 ± 6.6 |
| OXALIPLATIN | HYDROPHILIC *HYPERICUM* EXTRACT 30 mg/kg | 21.0 ± 2.0 | 42.0 ± 1.9* | 63.0 ± 1.9* | 14.5 ± 1.0 |

Oxaliplatin 2.4 mg/kg−1 for 5 consecutive days a week (15 i.p. injections - cumulative dose 36 mg/kg)

^ $P < 0.05$

\* $p > 0.01$

Example 2

Mononeuropathy Induced by Ligature of the Sciatic Nerve

Neuropathic pain is characterised by the development of an altered perception of pain, which is manifested as continuous spontaneous pain and hyperalgesia. In this model, the rats were anaesthetised with chloral hydrate 400 mg/kg i.p. or sodium pentobarbital 40 mg/kg i.p. The sciatic nerve was then exposed at thigh level by retracting the femoral biceps. Proximally to the trifurcation of the sciatic nerve, approx. 7 mm of nerve was released from the membranes and 4 loose ligatures were tied round the nerve, approx. 1 mm apart. In another group of animals an identical incision was made, but without the nerve ligature (sham operation). Neuropathy developed in 14 days. The tests with the potentially analgesic substances were performed on the 14th and 21st days after the operation using the paw pressure test (ref. 24).

The total freeze-dried extract at the dose of 10, 30, 60 and 100 mg/kg of body weight proved to be active to a statistically significant extent.

TABLE 2a

EFFECT OF *HYPERICUM* EXTRACT IN A RIGHT-SIDE MONONEUROPATHY MODEL IN RATS, EVALUATED WITH THE RAT PAW PRESSURE TEST

| TREATMENT i.p. | PAW | Pressure on rats' paws (g) | | | |
|---|---|---|---|---|---|
| | | Before treatment | After treatment | | |
| | | | 15 min | 30 min | 45 min |
| CMC | L | 60.5 ± 3.8 | 61.8 ± 3.7 | 64.6 ± 3.3 | 59.8 ± 3.2 |
| CMC | R | 22.8 ± 2.2 | 21.6 ± 3.5 | 23.0 ± 2.6 | 21.9 ± 3.7 |
| *HYPERICUM* EXTRACT 10 mg/kg | L | 56.2 ± 6.6 | 56.2 ± 7.2 | 58.7 ± 3.9 | 51.2 ± 4.3 |
| | R | 20.9 ± 4.0 | 22.5 ± 3.2 | 33.7 ± 4.7^ | 18.7 ± 2.4 |
| *HYPERICUM* EXTRACT 30 mg/kg | L | 63.3 ± 5.7 | 68.8 ± 4.4 | 73.3 ± 6.7 | 51.7 ± 7.5 |
| | R | 20.3 ± 4.4 | 59.8 ± 3.1 * | 65.5 ± 1.7 * | 31.3 ± 1.7 |
| *HYPERICUM* EXTRACT 60 mg/kg | L | 62.6 ± 3.0 | 68.5 ± 4.1 | 77.6 ± 4.3 | 60.7 ± 2.2 |
| | R | 21.9 ± 2.4 | 37.0 ± 2.8^ | 41.8 ± 4.4 * | 22.7 ± 2.4 |
| *HYPERICUM* EXTRACT 100 mg/kg | L | 62.8 ± 1.7 | 72.2 ± 2.4 | 78.6 ± 2.0 | 62.5 ± 3.8 |
| | R | 21.3 ± 2.7 | 27.5 ± 4.3 | 31.5 ± 4.3 * | 20.5 ± 2.9 |

^ $P < 0.05$

\* $p > 0.01$

The freeze-dried extract of the hydrophilic fraction at the doses of 10, 30, 60 and 100 mg/kg of body weight proved active to a statistically significant extent, as shown in Table 2b below.

TABLE 2 b

EFFECT OF HYDROPHILIC FRACTION OF *HYPERICUM* EXTRACT IN A RIGHT-SIDE MONONEUROPATHY MODEL IN RATS, EVALUATED WITH THE RAT PAW PRESSURE TEST

| TREATMENT | | BEFORE | Pressure on rats' paws (g) | | |
|---|---|---|---|---|---|
| | | | AFTER TREATMENT | | |
| MG/KG P.O. | PAW | TREATMENT | 15 min | 30 min | 45 min |
| CMC | L | 60.5 ± 3.8 | 61.8 ± 3.7 | 64.6 ± 3.3 | 59.8 ± 3.2 |
| CMC | R | 22.8 ± 2.2 | 21.6 ± 3.5 | 23.0 ± 2.6 | 21.9 ± 3.7 |
| HYDROPHILIC *HYPERICUM* EXTRACT 10 mg/kg | L | 60.9 ± 4.7 | 62.5 ± 5.8 | 61.3 ± 6.0 | 58.2 ± 3.0 |
| | R | 20.3 ± 2.9 | 33.5 ± 3.3 | 41.6 ± 3.5 * | 19.8 ± 6.0 |
| HYDROPHILIC *HYPERICUM* EXTRACT 30 mg/kg | L | 59.4 ± 4.6 | 67.5 ± 4.8 | 63.6 ± 2.4 | 58.7 ± 3.1 |
| | R | 22.3 ± 2.4 | 55.1 ± 3.2 * | 62.0 ± 3.5 * | 26.5 ± 3.3 |
| HYDROPHILIC *HYPERICUM* EXTRACT 60 mg/kg | L | 60.4 ± 3.6 | 65.8 ± 2.0 | 71.2 ± 3.7 | 57.7 ± 4.8 |
| | R | 20.2 ± 2.3 | 52.4 ± 3.7 * | 59.7 ± 3.0 * | 24.5 ± 3.2 |
| HYDROPHILIC *HYPERICUM* EXTRACT 100 mg/kg | L | 63.7 ± 3.5 | 71.2 ± 4.3 | 73.0 ± 2.9 | 61.2 ± 3.1 |
| | R | 23.5 ± 3.9 | 30.2 ± 3.4 | 35.8 ± 2.5 * | 20.3 ± 3.3 |

^ $P < 0.05$
\* $p > 0.01$

Example 3

Paclitaxel-Induced Neuropathy

The total freeze-dried extract at the doses of 30 and 100 mg/kg of body weight and the extract of the hydrophilic fraction at the dose of 30 mg/kg proved active to a statistically significant extent in the paclitaxel-induced neuropathic pain test (Ref 25)

TABLE 3

EFFECT OF *HYPERICUM* EXTRACT (30 and 100 mg/kg$^{-1}$ p.o.) AND THE HYDROPHILIC FRACTION ON PACLITAXEL-INDUCED HYPERALGESIA IN THE RAT PAW PRESSURE TEST

| TREATMENT i.p. | TREATMENT p.o. | Pressure on rats' paws (g) | | | |
|---|---|---|---|---|---|
| | | Before treatment | | | |
| | | Pre-test | 15 min | 30 min | 45 min |
| SALINE | SALINE | 57.2 ± 3.9 | 62.6 ± 4.4 | 58.3 ± 4.7 | 56.9 ± 3.9 |
| PACLITAXEL | SALINE | 43.7 ± 4.2 | 39.6 ± 3.8 | 41.9 ± 4.3 | 42.5 ± 4.9 |
| SALINE | *HYPERICUM* EXTRACT 30 mg/kg BATCH 7I0525 | 62.6 ± 3.3 | 59.8 ± 4.4 | 57.6 ± 4.7 | 60.1 ± 4.6 |
| PACLITAXEL | *HYPERICUM* EXTRACT 30 mg/kg BATCH 7I0525 | 40.5 ± 3.8 | 50.3 ± 3.4 * | 48.0 ± 4.0 | 36.6 ± 4.2 |
| PACLITAXEL | *HYPERICUM* EXTRACT 100 mg/kg BATCH 7I0525 | 39.6 ± 3.3 | 51.6 ± 3.1 * | 46.3 ± 3.9 | 39.5 ± 4.0 |
| PACLITAXEL | HYDROPHILIC FRACTION 30 mg/kg BATCH 7I0660 | 38.3 ± 3.9 | 49.2 ± 3.8 * | 44.0 ± 3.5 | 33.8 ± 3.7 |

Treatment: Paclitaxel 0.5 mg/kg$^{-1}$ was injected i.p. for four days (days 1, 3, 5 and 8). The cumulative dose of Paclitaxel was 2.0 mg/kg$^{-1}$. The test was performed 14-15 days after the last injection of paclitaxel. Vehicle: Saline: ethylene oxide 9:1 8 rats per group (two experiments).
^ $P < 0.05$; versus rats treated with paclitaxel.

Example 4

Vincristine-Induced Hyperalgesia

A reduction in the pain threshold was obtained in the rat by i.v. administration of vincristine (150 gamma/kg i.v. every 2 days for 5 days until the cumulative dose of 750 gamma/kg was reached); the test (paw-pressure) was conducted 4 days after the last injection (Ref 26). Alternatively, the vincristine was applied (brushed) directly onto the sciatic nerve. The total freeze-dried extract at the doses of 30 and 100 mg/kg of body weight and the freeze-dried extract of the hydrophilic fraction at the dose of 30 mg/kg proved active to a statistically significant extent.

TABLE 4

EFFECT OF *HYPERICUM* EXTRACT (30 and 100 mg kg−1 p.o.)
AND THE HYDROPHILIC FRACTION ON VINCRISTINE-INDUCED
HYPERALGESIA IN THE RAT PAW PRESSURE TEST

| TREATMENT mg kg−1 i.v. | TREATMENT mg kg−1 p.o. | Pressure on rats' paws (g) | | | | |
|---|---|---|---|---|---|---|
| | | | Before treatment | | | |
| | | Pre-test | 15 min | 30 min | 45 min | 60 min |
| SALINE | SALINE | 61.6 ± 3.3 | 57.2 ± 4.5 | 62.4 ± 4.0 | 58.3 ± 4.1 | 61.6 ± 5.3 |
| VINCRISTINE | SALINE | 35.2 ± 3.4 | 33.8 ± 4.5 | 35.1 ± 3.6 | 36.2 ± 3.7 | 34.9 ± 2.8 |
| SALINE | *HYPERICUM* EXTRACT 30 mg/kg BATCH 7I0525 | 56.3 ± 3.3 | 63.4 ± 4.0 | 61.6 ± 3.8 | 57.3 ± 4.4 | 58.7 ± 3.3 |
| VINCRISTINE | *HYPERICUM* EXTRACT 30 mg/kg BATCH 7I0525 | 34.9 ± 3.1 | 52.6 ± 4.2* | 51.9 ± 4.5* | 38.3 ± 5.0 | 34.9 ± 5.2 |
| VINCRISTINE | *HYPERICUM* EXTRACT 100 mg/kg BATCH 7I0525 | 33.90 ± 3.5 | 48.2 ± 4.1* | 47.5 ± 4.7* | 35.7 ± 4.1 | |
| VINCRISTINE | *HYPERICUM* EXTRACT 30 mg/kg BATCH 7I0660 | 31.5 ± 3.2 | 50.9 ± 3.7* | 53.4 ± 4.2* | 36.5 ± 4.9 | 31.3 ± 3.8 |

Treatment with vincristine: five i.v. injections of 150 μg/kg$^{-1}$ performed every 2 days up to a cumulative dose of 750 μg/kg$^{-1}$ i.v.
The test was performed 4 days after the last injection of vincristine. 7-8 rats per group (two experiments).
^P < 0.05
*P < 0.01 versus rats treated with vincristine
14 rats per group (two experiments).
*P > 0.05 versus rats treated with vincristine.

Example 5

Hypericin in Oxaliplatin-Induced Neuropathy

Using the same method as in Example 1, the following results were obtained by administering hypericin at the doses indicated in Table 5.

TABLE 5

EFFECT OF HYPERICIN (single administration) ON OXALIPLATIN-
INDUCED HYPERALGESIA IN THE RAT PAW PRESSURE TEST

| TREATMENT i.p. | TREATMENT p.o. | Pressure on rats' paws (g) | | | | | |
|---|---|---|---|---|---|---|---|
| | | | Treatment period (weeks of oxaliplatin) | | | | |
| | | Pre-test before all treatments | 3rd week Pre-test | 3rd week + 15 min | 3rd week + 30 min | 3rd week + 45 min | 3rd week + 60 min |
| SALINE | SALINE | 60.1 ± 2.2 | 66.2 ± 4.5 | 65.0 ± 4.3 | 63.9 ± 3.8 | 66.5 ± 4.4 | 68.1 ± 4.1 |
| OXALIPLATIN | SALINE | 58.4 ± 4.6 | 30.5 ± 4.7 | 28.4 ± 4.1 | 25.8 ± 3.6 | 27.1 ± 4.1 | 29.1 ± 2.8 |
| OXALIPLATIN | HYPERICIN 0.11 mg/kg + CMC | 63.2 ± 3.5 | 32.4 ± 2.0 | 44.1 ± 2.8* | 55.0 ± 2.2* | 53.3 ± 2.6* | 31.3 ± 3.0 |

TABLE 5-continued

EFFECT OF HYPERICIN (single administration) ON OXALIPLATIN-INDUCED HYPERALGESIA IN THE RAT PAW PRESSURE TEST

| | | Pressure on rats' paws (g) | | | | | |
|---|---|---|---|---|---|---|---|
| | | | Treatment period (weeks of oxaliplatin) | | | | |
| TREATMENT i.p. | TREATMENT p.o. | Pre-test before all treatments | 3rd week Pre-test | 3rd week + 15 min | 3rd week + 30 min | 3rd week + 45 min | 3rd week + 60 min |
| OXALIPLATIN | HYPERICIN 0.11 mg/kg + HYPERISIDE 3.118 mg/kg | 60.6 ± 3.8 | 31.7 ± 2.5 | 56.3 ± 2.6* | 58.5 ± 2.7* | 52.5 ± 1.2* | 33.0 ± 2.8 |

Treatment: Oxaliplatin 2.4 mg kg$^{-1}$ for 5 consecutive days a week (15 i.p. injections - cumulative dose 36 mg/kg)
8 rats per group (two experiments).
*P < 0.01

Example 6

Hypericin in Neuropathy Induced by Ligature of the Sciatic Nerve

Using the same method as in Example 2, the following results were obtained by administering hypericin at the doses indicated in Table 6.

TABLE 6

EFFECT OF HYPERICIN IN A RIGHT-SIDE MONONEUROPATHY MODEL IN THE RAT, EVALUATED WITH THE RAT PAW PRESSURE TEST

| | | | Paw | | | |
|---|---|---|---|---|---|---|
| Treatment | | Before | After treatment | | | |
| MG/KG. P.O. | PAW | treatment | 15 min | 30 min | 4 min | 60 min |
| CMC | L | 60.8 ± 2.9 | 57.8 ± 3.3 | 57.4 ± 3.8 | 59.2 ± 4.9 | 55.9 ± 3.8 |
| CMC | R | 23.2 ± 2.2 | 24.7 ± 3.5 | 22.9 ± 2.8 | 23.6 ± 3.7 | 20.7 ± 3.5 |
| HYPERICIN 0.11 mg/kg | L | 21.6 ± 2.7 | 23.8 ± 3.3 | 22.7 ± 2.1 | 24.8 ± 3.9 | 21.5 ± 3.0 |
| HYPERICIN 0.11 mg/kg | R | 24.3 ± 4.6 | 28.1 ± 1.2 | 43.7 ± 2.0* | 41.6 ± 2.7* | 25.9 ± 2.2 |

The doses of hypericin, hyperoside and amentoflavone corresponded to 30 mg/kg p.o. of hydrophilic fraction of *hypericum* extract - batch 070305/I)
^P < 0.05;
*P < 0.01.
Each value represents the mean of 8 rats.

Example 7

Effect of Freeze-Dried *Hypericum* Extract and Hypericin in Pain Caused by Monosodium Iodoacetate-Induced Osteoarthritis The reduction in the pain threshold was induced by a single administration of monoiodoacetate (MIA) into the paw joint of the rat (Ref. 27).

TABLE 7

EFFECT OF HYPERICIN AND *HYPERICUM* EXTRACT ON PAIN INDUCED BY OSTEOARTHRITIS OF THE KNEE, EVALUATED IN THE RAT PAW PRESSURE TEST

| TREAT-MENT | TREATMENT | After treatment | | | | |
|---|---|---|---|---|---|---|
| | mg kg–1 p.o. | Pre-test | 15 min | 30 min | 45 min | 60 min |
| SALINE | CMC | 63.9 ± 3.3 | 64.6 ± 2.5 | 60.5 ± 3.8 | 62.6 ± 3.7 | 64.6 ± 4.0 |
| MIA | CMC | 22.6 ± 2.9 | 20.3 ± 4.1 | 24.9 ± 2.7 | 23.2 ± 3.5 | 24.0 ± 2.7 |

TABLE 7-continued

EFFECT OF HYPERICIN AND *HYPERICUM* EXTRACT
ON PAIN INDUCED BY OSTEOARTHRITIS OF THE KNEE,
EVALUATED IN THE RAT PAW PRESSURE TEST

| TREAT-MENT | TREATMENT mg kg–1 p.o. | Pre-test | After treatment | | | |
|---|---|---|---|---|---|---|
| | | | 15 min | 30 min | 45 min | 60 min |
| MIA | HYPERICIN 0.11 mg/kg | 23.4 ± 3.3 | 45.9 ± 2.7* | 49.7 ± 3.8* | 42.8 ± 3.9* | 31.7 ± 3.5 |
| MIA | HYPERICUM EXTRACT 60 mg/kg BATCH 7I0525 | 21.1 ± 2.1 | 39.7 ± 3.1* | 42.7 ± 2.1* | 38.4 ± 3.3* | 22.1 ± 3.0 |

Treatment: Monosodium iodoacetate (MIA) 2 mg in a volume of 25 μl was injected into the antechamber of the left knee of non-anaesthetised rats.
Each value represents the mean of 2 experiments (11 rats).
^P < 0.05;
*P < 0.01 by comparison with rats treated with MIA/CMC.
*Fernihough J. et al. Pain* 112: 83-93 (2004).

REFERENCES

1. Nanna B et al "An evidence-based algorithm for the treatment of neuropathic pain" Medscape General Medicine 2007; 9(2):36.
2. Bridges D, Thompson S W, Rice A S. Mechanisms of neuropathic pain. Br J Anaesth. 2001; 87(1):12-26. Review.
3. Andrés J. D.; Garcia-Ribas G. Neuropathic Pain Treatment: The Challenge Pain Practice: 2003, 3, (1): 1-7.
4. Fernihough J, Gentry C, Malcangio M, Fox A, Rediske J, Pellas T, Kidd B, Bevan S, Winter J. Pain related behaviour in two models of osteoarthritis in the rat knee. Pain. 2004 November; 112(1-2):83-93.
5. Jackson K C 2nd. Pharmacotherapy for neuropathic pain. Pain Pract. 2006 March; 6(1):27-33.
6. Dworkin R H, Backonja M, Rowbotham M C, Allen R R, Argoff C R, Bennett G J, Bushnell M C, Farrar J T, Galer B S, Haythornthwaite J A, Hewitt D J, Loeser J D, Max M B, Saltarelli M, Schmader K E, Stein C, Thompson D, Turk D C, Wallace M S, Watkins L R, Weinstein S M. Advances in neuropathic pain: diagnosis, mechanisms, and treatment recommendations. Arch Neurol. 2003; 60(11):1524-34.
7. Taylor R S. Epidemiology of refractory neuropathic pain. Pain Pract. 2006 March; 6(1):22-6.
8. Butterweck V. Mechanism of action of St John's Wort in depression: what is known? CNS Drugs. 2003; 17(8):539-62.
9. Rodríguez-Landa J F, Contreras C M. A review of clinical and experimental observations about antidepressant actions and side effects produced by *Hypericum perforatum* extracts. Phytomedicine. 2003 November; 10(8):688-99.
10. Mennini T, Gobbi M. The antidepressant mechanism of *Hypericum perforatum*. Life Sci. 2004 Jul. 16; 75(9):1021-7.
11. No authors listed] Monograph. *Hypericum perforatum*. Altern Med Rev. 2004 September; 9(3):318-25.
12. Di Carlo G, Borrelli F, Ernst E, Izzo A A. St John's Wort: Prozac from the plant kingdom. Trends Pharmacol Sci. 2001 June; 22(6):292-7.
13. Müller W E. Current St John's Wort research from mode of action to clinical efficacy. Pharmacol Res. 2003 February; 47(2):101-9.
14. Nöldner M, Schötz K. Rutin is essential for the antidepressant activity of *Hypericum perforatum* extracts in the forced swimming test. Planta Med. 2002 July; 68(7):577-80.
15. Butterweck V, Christoffel V, Nahrstedt A, Petereit F, Spengler B, Winterhoff H. Step by step removal of hyperforin and hypericin: activity profile of different *Hypericum* preparations in behavioral models. Life Sci. 2003 Jun. 20; 73(5):627-39.
16. Sindrup S H, Madsen C, Bach F W, Gram L F, Jensen T S. St. John's Wort has no effect on pain in polyneuropathy. Pain. 2001 April; 91(3):361-5.
17. Sánchez-Mateo C C, Bonkanka C X, Hernández-Perez M. Rabanal R M. Evaluation of the analgesic and topical anti-inflammatory effects of *Hypericum reflexum* L. fil. J. Ethnopharmacol. 2006; 11:107(1):1-6.
18. Trovato A, Raneri E, Kouladis M, Tzakou O, Taviano M F, Galati E M. Anti-inflammatory and analgesic activity of *Hypericum empetrifolium* Willd. (Guttiferae). Farmaco. 2001; 56(5-7):455-7.
19. Viana A F, Heckler A P, Fenner R. Rates S M. Antinociceptive activity of *Hypericum caprifoliatum* and *Hypericum polyanthemum* (Guttiferae). Braz J Med Biol Res. 2003:36(5):631-4.
20. Rabanal R M, Bonkanka C X, Hernandez-Perez M, Sanchez-Mateo C C. Analgesic and topical anti-inflammatory activity of *Hypericum canariense* L. and *Hypericum glandulosum* Ait. J. Ethnopharmacol. 2005 Jan. 15; 96(3): 591-6.
21. Bukhari I A, Dar A, Khan R A. Antinociceptive activity of methanolic extracts of St. John's Wort (*Hypericum perforatum*) preparation. Pak J Pharm Sci. 2004; 17(2):13-9.
22. Abdel-Salam O M Anti-inflammatory, antinociceptive, and gastric effects of *Hypericum perforatum* in rats. Scientific World Journal. 2005 Aug. 8; 5: 586-95.
23. Cavaletti U, Tredici G, Petruccioli M G, Donde F, Tredici P, Marmiroli P, Minoia C, Ronchi A, Bayssas M, Etienne G G. Effects of different schedules of oxaliplatin treatment on the peripheral nervous system of the rat. Eur J. Cancer. 2001; 37(18):2457-63.
24. Bennett G J, Xie Y K. A peripheral mononeuropathy in rat that produces disorders of pain sensation like those seen in man. Pain. 1988; 33(1):87-107.
25. Polomano R C, Mannes A J, Clark U S, Bennett G J. A painful peripheral neuropathy in the rat produced by the chemotherapeutic drug, paclitaxel. Pain. 2001 December; 94(3):293-304.
26. Aley K O, Reichling D B, Levine J D. Vincristine hyperalgesia in the rat: a model of painful vincristine neuropathy in humans. Neuroscience. 1996 July; 73(1):259-65.

27. Fernihough J, Gentry C, Malcangio M, Fox A, Rediske J, Pellas T, Kidd B, Bevan S, Winter J. Pain related behaviour in two models of osteoarthritis in the rat knee. Pain. 2004 November; 112(1-2):83-93.
28. Irwin S. Comprehensive observational assessment: Ia. A systematic, quantitative procedure for assessing the behavioral and physiologic state of the mouse. Psychopharmacologia. 1968 Sep. 20; 13(3):222-57.
29. Vaught J L, Pelley K, Costa L G, Setler P, Enna S J. A comparison of the antinociceptive responses to the GABA-receptor agonists THIP and baclofen. Neuropharmacology. 1985 March; 24(3):211-6.

The invention claimed is:

1. A method of treating neuropathic pain, the method comprising administering orally to a subject a composition comprising an effective amount of a hydrophilic fraction of an extract of *hypericum* flowering stems containing hypericin.

2. The method of claim 1, wherein the neuropathic pain is caused by treatment with chemotherapy drugs.

3. The method of claim 2, wherein the chemotherapy drugs are platinum complexes, vincristine and paclitaxel.

4. The method of claim 1, wherein the neuropathic pain derives from sciatic pain.

5. The method of claim 1, wherein the neuropathic pain derives from osteoarthritis.

6. The method of claim 1, wherein the composition comprises a naphthodianthrone derivative content of not less than 0.25% by weight, wherein the naphthodianthrone derivative is selected from the group consisting of hypericin, pseudohypericin, and isohypericin.

7. The method of claim 1, wherein the extract is freeze-dried.

8. The method of claim 7, wherein the extract is a water-alcohol or water-acetone extract.

9. The method of claim 1, wherein the flowering stems are from *Hypericum perforatum* L.

10. A method of treating neuropathic pain caused by treatment with a chemotherapy drug, the method comprising administering orally to a subject a composition comprising an effective amount of a hydrophilic component of *hypericum* flowering stems containing hypericin.

11. The method of claim 10, wherein the chemotherapy drug is selected from the group consisting of platinum complexes, vincristine and paclitaxel.

12. The method of claim 10, wherein the composition comprises a naphthodianthrone derivative content of not less than 0.25% by weight, wherein the naphthodianthrone derivative is selected from the group consisting of hypericin, pseudohypericin, and isohypericin.

13. The method of claim 10, wherein the extract is freeze-dried.

14. The method of claim 13, wherein the extract is a water-alcohol or water-acetone extract.

15. The method of claim 10, wherein the flowering stems are from *Hypericum perforatum* L.

\* \* \* \* \*